United States Patent [19]

Metzger et al.

[11] Patent Number: 5,432,157
[45] Date of Patent: Jul. 11, 1995

[54] CHRYSOSPERMINS, ACTIVE PEPTIDES FROM APIOCREA CHRYSOSPERMA HAVING A PHARMACOLOGICAL EFFECT AND A USE THEREOF

[75] Inventors: Jörg Metzger, Tübingen; Brigitte Schlegel, Jena; Werner F. Fleck, Erfurt; Klausjürgen Dornberger, Jena; Wolfgang Ihn, Jena; Wolfgang Schade, Jena; Udo J. Gräfe, Jena, all of Germany

[73] Assignee: Hoechst Aktiengesellschaft, Frankfurt am Main, Germany

[21] Appl. No.: 198,567

[22] Filed: Feb. 18, 1994

[30] Foreign Application Priority Data

Feb. 20, 1993 [DE] Germany .................. 43 05 352.1

[51] Int. Cl.⁶ .................. A61K 38/00; C07K 5/00; C07K 7/00; C07K 17/00
[52] U.S. Cl. .................. 514/13; 530/326
[58] Field of Search .................. 514/13; 530/326

[56] References Cited

PUBLICATIONS

Bruckner et al., "The Sequences of the Membrane-Modifying Peptide Antibotic Trichotoxin A-40," Angew. Chem. Int. Ed. Engl. 18(6):476-477 (1979).
Przybylski et al., "Elucidation of Structure and Microheterogeneity of the Polypeptide Antibiotics Paracelsin and Trichotoxin A-50 by Fast Atom Bombardment Mass Spectrometry in Combination with Selective in situ Hydrolysis," Biomedical Mass Spectrometry, 11(11):569-582 (1984).

*Primary Examiner*—Jill Warden
*Assistant Examiner*—Sheela J. Huff
*Attorney, Agent, or Firm*—Finnegan, Henderson Farabow, Garrett & Dunner

[57] ABSTRACT

The invention relates to the chrysospermin active peptides of the formula I

AcPhe-Aib-Ser-Aib-x-Leu-Gln-Gly-Aib-Aib-Ala-Ala-Aib-Pro-y-Aib-Aib-Gln-Trp-ol (SEQ ID NO. 1)

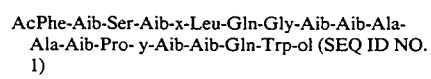

in which x and y, independently of each other, denote Aib or Iva, which are synthesized by the fungus *Apiocrea chrysosperma* during fermentation and which accumulate in the culture broth, to a preparation process, to the use of the chrysospermins as pharmacological active compounds, in particular as active compounds against bacteria, fungi and/or nematodes, and for the treatment of rejection reactions in organ transplantations and of tumor disorders, and to the microorganism *Apiocrea chrysosperma* DSM 7444.

3 Claims, No Drawings

CHRYSOSPERMINS, ACTIVE PEPTIDES FROM APIOCREA CHRYSOSPERMA HAVING A PHARMACOLOGICAL EFFECT AND A USE THEREOF

The invention relates to the active peptides chrysospermins, which are synthesized during fermentation by the fungus *Apiocrea chrysosperma* and accumulate in the culture broth, to a process for their preparation, to the use of the chrysospermins as pharmacological active compounds, in particular as an active compound against bacteria, fungi and/or nematodes as well as for the treatment of rejection reactions in organ transplantations and of neoplastic disorders, and to the microorganism Apiocrea chrysosperma DSM 7444.

Peptides possessing up to 20 amino acids, some of which are structurally unusual, are produced by bacteria and fungi by way of their secondary metabolism using nonribosomal peptide synthetases. Many of the previously known secondary metabolites having a peptide structure possess interesting biological effects as antibiotics, enzyme inhibitors, cardiotonic agents, immunomodulators, insecticides, nematocides, etc. (see, e.g., Gräfe, U. Biochemie der Antibiotika (Biochemistry of Antibiotics), Spektrum Heidelberg, 1992; Sasaki et al., J. Antibiot., 45, 692 to 697, 1992; Hamano et al., J. Antibiot., 45, 899 to 905, 1992; Tomoda et al., J. Antibiot., 45, 1207 to 1215, 1992.

Pharmacologically active secondary metabolites can be detected with the aid of biological screening processes; for example, the formation of pigments can be stimulated in strains of the genus Phoma. (Hübner, R.; Schlegel, B.; Fleck, W. F.: Fungal cells as screening models for microbial metabolites affecting differentiation; p. 90 in: Abstracts of 2nd International Bioactive Metabolites from Microorganisms, May 2 to 7, 1988 Gera, FRG).

Within the structural class of the active peptides, the so-called peptaibols (peptaibophols in the presence of phenylalaninol as the C-terminal substituent) are notable for the fact that they contain an unusually large number of amino acids (up to 20, including a high proportion of alpha-aminoisobutyric acid) (Brückner, H., König, W. A., Greiner, M., Jung, G. Angew. Chem. Int. Ed. Engl. 18 (1979), 476 to 477).

Some representatives of the peptaibophols of the alamethicin/suzukacillin type (alamethicins, suzukacillin, paracelcins, hypelcin, trichotoxin, antiamoabin, emerimycin, cerexins, zervamicin and trichorzianins) have been demonstrated to possess antibacterial, antifungal, antiprotozoal and nematocidal activities, as well as antitumorigenic, antiinflammatory, hemolytic and antihelmintic effects, and to promote the formation of helically organized ion channels in biological membranes. (Gale, E. F. et al. in: The Molecular Basis of Antibiotic Action J. Wiley, N.Y., Sydney, Toronto; 1981; Bycroft, B. W.: Dictionary of Antibiotics and Related Substances Chapman and Hall, London, N.Y. 1988).

However the previously known active peptides often possess disadvantages which are expressed in the form of an unsatisfactory level of efficacy, in a high level of toxicity and/or in undesirable side effects.

To date, there are few descriptions of active peptides possessing up to 20 amino acids, some of which are unusual, having effects as antitumorigenic agents. Many of the known antitumorigenic agents give rise, as side effects during therapy, to nausea, vomiting and diarrhoea which also necessitate medical treatment in hospital. In addition, these pharmaceuticals also alter the speed of growth of other cells occurring in the body, leading in turn to symptoms such as, for example, loss of hair or anemia. It is also not previously known to employ these peptides as active compounds or pharmaceuticals for the treatment of rejection reactions. In 1990, 15,000 organ transplantations were carried out in the USA. The majority of the transplantations concerned the kidney, but heart, skin, lung, liver and pancreas are also being transplanted to an increasing degree. In many of the patients receiving transplants, a rejection reaction occurs in the body against the organ which has been transferred from another person. Three forms of rejection reaction are distinguished: i.e. hyperacute, acute and chronic rejection.

Hyperacute rejection is in the main brought about by antibodies circulating in the blood, which antibodies are directed against the tissue of the transferred organ (transplant) and lead in a very short space of time—frequently in minutes—to necroses in the transplant.

The object of the invention is to seek novel microbial active peptides possessing improved properties and novel mechanisms of effect.

In accordance with the invention, this object is achieved by fermenting *Apiocrea chrysosperma* in a nutrient solution containing carbon and nitrogen sources and the customary inorganic salts until the chrysospermin active peptides accumulate in the culture, and then isolating the chrysospermins from the culture broth and, where appropriate, fractionating the chrysospermins into chrysospermins A, B, C and D. The active peptides possess pharmacological activity and can be employed, in particular, as active compounds against bacteria, fungi and/or nematodes, as well as for the treatment of rejection reactions associated with organ transplantations and of neoplastic disorders.

The invention consequently relates to:

1. A compound of the formula I

AcPhe-Aib-Ser-Aib-x-Leu-Gln-Gly-Aib-Aib-Ala-Ala-Aib-Pro-y-Aib-Aib-Gln-Trp-ol (SEQ ID NO: 1)

in which x and y, independently of each other, denote Aib or Iva.

2. A process for the preparation of a compound of the formula I, wherein *Apiocrea chrysosperma* is cultivated in a nutrient medium until a compound of the formula I accumulates in the culture broth, and this compound is isolated from the culture broth.

3. A use of a compound of the formula I as a pharmacologically active compound.

4. *Apiocrea chrysosperma* DSM 7444.

The invention is described in detail below, in particular in its preferred embodiments. In addition, it is determined by the content of the patent claims.

Terms and abbreviations are defined as follows:

Compounds of the formula I are also designated chrysospermins or active peptides.

The nutrient medium containing the fungal mycelium which has grown in it is designated the culture broth.

AcPhe stands for N-acetylphenylalanine, Aib stands for α-aminobutyric acid, Iva stands for isovaline and Trp-ol stands for tryptophanol.

Chrysospermin A (1896 Daltons) denotes a compound of the formula I in which Aib is present at positions x and y.

Chrysospermin B (1910 Daltons) denotes a compound of the formula I in which Aib is present at position x and Iva is present at position y.

Chrysospermin C (1910 Daltons) denotes a compound of the formula I in which Iva is present at position x and Aib is present at position y.

Chrysospermin D (1924 Daltons) denotes a compound of the formula I in which Iva is present at positions x and y.

The term organ is understood to mean all the organs in mammals, in particular those of man, for example kidney, heart, skin, liver, pancreas, muscle, bone, intestine or stomach, as well as blood or hair.

Rejection reactions mean all the defensive measures of the recipient organism which lead in the end to destruction of the cells or tissue of the transferred organ or which impair the viability of the transferred organ.

Chrysospermins are produced by *Apiocrea chrysosperma*, preferably *Apiocrea chrysosperma* DSM 7444.

*Apiocrea chrysosperma* (older designation Hypomyces chrysospermus, in: Compendium of Soil Fungi, K. H. Domsch, W. Gams and T.-H. Anderson (eds.) Academic Press, vol. 1, 398 to 399) is very widespread in temperate climatic zones as a parasitic microorganism in the fruiting bodies of Boletales and is obtained from soil samples. Morphologically, the anamorphic form of *Apiocrea chrysosperma sperma* is notable for branched conidiophores, yellowish, round, occasionally also blastic, conidia, which occur in large numbers wart-shaped or spiny conidia possessing a thick, multilayered wall.

Pure cultures can be isolated from such soil samples by methods familiar to the person skilled in the art by setting up dilution series, and plating out and incubating on nutrient agar media.

Using sequential isolation steps, a fungal colony can be isolated from *Apiocrea chrysosperma* which very efficiently accumulates the chrysospermin active peptides in the culture broth.

The strongly-producing fungal colony is propagated. An isolate of *Apiocrea chrysosperma* DSM 7444 was deposited with the Deutsche Sammlung von Mikroorganismen und Zellkulturen GmbH (German collection of microorganisms and cell cultures), Marschroder Weg 1B, 3300 Braunschweig, Germany, in accordance with the stipulations of the Budapest treaty of the 28.01.1993.

When cultivated on agar nutrient bases containing glucose and malt extract as the carbon source and yeast extract as the nitrogen source, the mycelium of the fungus is white after 14 days of incubation at 25° C., and then subsequently golden yellow, with conidia of a truncated wart shape being present. The teleomorphic form is not produced in the culture.

*Apiocrea chrysosperma*, preferably *Apiocrea chrysosperma* DSM 7444, produce active peptides of the general formula I in a nutrient medium containing a carbon source, a nitrogen source and the customary mineral salts. Instead of the strain itself, mutants and variants of *Apiocrea chrysosperma* DSM 7444 can naturally also be employed.

All those microorganisms of the species which are able to synthesize the chrysospermin active peptides are regarded as mutants and variants.

Such mutants can be produced, in a manner known per se, by physical means, for example by irradiation with ultraviolet or X-rays, or with chemical mutagens, such as, for example, ethyl methanesulfonate (EMS), 2-hydroxy-4-methoxybenzophenone (MOB) or N-methyl-N'-nitro-N-nitrosoguanidine (MNNG).

Screening for mutants and variants which synthesize a compound of the general formula I is effected by determining pigment formation in test organisms of the genus Phoma, preferably Phoma sp., particularly preferably *Phoma destructiva*, which formation is stimulated by the active peptides of the general formula I which are secreted into the supernatant.

Alternatively, the biological activity of the active peptides secreted into the supernatant can also be assessed by testing their antibiotic effects on known test organisms using methods familiar to the person skilled in the art.

Carbohydrate-containing natural products, such as malt extract, as well as assimilable carbohydrates and alcohols, such as, for example, glucose, lactose and glycerol, or their mixtures in arbitrary proportions, are suitable for use as preferred carbon sources for the aerobic fermentation.

Amino acids, peptides and proteins, as well as their degradation products such as tryptones or peptones, are suitable for use as the nitrogen source as are meat extracts, ground seeds, for example from corn, wheat, beans, soya bean or the cotton plant, distillation residues from the preparation of alcohol, meat meals or yeast extracts, as well as ammonium salts and nitrates.

The formation of a compound of the general formula I is effected particularly favorably in nutrient media which contain 0.2 to 6% of malt extract, preferably 2 to 4% of malt extract, and 0.01 to 1% of yeast extract, preferably 0.1 to 0.4% of yeast extract.

Cultivation is effected aerobically, for example in a submerged manner with shaking and stirring in shaking flasks, preferably, however, on the surface as a stationary culture. It is carried out in a temperature range of between 15° and 35° C., preferably of between 23° and 33° C., particularly preferably of between 27° and 30° C.

The pH is between 4 and 7, preferably between 5.5 and 6.5.

The microorganism is cultivated under these conditions for 5 to 21 days, preferably 7 to 18 days.

The fermentation can be carried out on a laboratory scale (culture volumes of between 100 ml and 200 l) as well as on a production scale (volumes of up to several $m^3$).

Advantageously, the cultivation is carried out in several steps, i.e. one or more precultures are first prepared in a liquid nutrient medium, which precultures are then inoculated into the actual production medium, the main culture, for example in the ratio 1:20.

The preculture is obtained by transferring a sporulated mycelium from malt agar nutrient bases, for example, into a nutrient solution, for example by inoculating agar pieces which are overgrown with mycelium, and then incubating these pieces for 11 to 21 days, preferably 15 to 18 days.

The sporulated mycelium can be obtained, for example, by allowing the strain to grow for about 11 to 21 days, preferably 15 to 18 days, on a solid nutrient base, e.g. malt agar.

The course of the fermentation and the appearance of the active peptides can be monitored in accordance with chromatographic methods which are known to the person skilled in the art, such as, for example, thin layer chromatography (TLC) or high performance liquid chromatography (HPLC), or by testing the biological activity towards test organisms.

The active peptides of general formula I are contained in the culture broth, preferably in the mycelium.

The active peptides are isolated from the culture medium by known methods, taking into account the chemical, physical and biological properties of the products.

Thin layer chromatography, for example on silica gel using chloroform/methanol mixtures as the eluent, can be used for testing the concentration of active compound in the culture medium or in the individual isolation steps. In the thin-layer chromatographic fractionation, detection can take place, for example, by means of coloring reagents, such as 2% vanillin/conc. sulfuric acid.

In order to isolate the active peptides, the culture broth and mycelium are extracted at the end of the fermentation once to five times, preferably three times, with organic lipophilic solvents, such as ethyl acetate and butyl acetate or dichloromethane, preferably ethyl acetate.

After concentrating the extract and precipitating out the chrysospermins A, B, C and D with aliphatic hydrocarbons such as n-hexane or n-heptane, the chrysospermins are separated chromatographically using customary chromatographic adsorbents and carrier materials, such as, for example, silica gels or organophilic dextran gels. The sequential use of column chromatography on silica gel or gel chromatography on organophilic dextran gels results in a mixture of chrysospermins A, B, C and D (molar masses 1896, 1910, 1910 and 1924 Daltons, respectively). Fractionation into the individual components is effected by means of preparative high performance liquid chromatography (HPLC).

The chemical identity of the chrysospermin active peptides A, B, C and D, which are formed by *Apiocrea chrysosperma*, preferably *Apiocrea chrysosperma* DSM 7444, is confirmed unequivocally by chemical degradation and analysis of the amino acids which have been formed, by mass spectroscopy (FAB-MS, electrospray-MS, MS-MS) and by NMR investigations.

The antibacterial and/or antifungal effects can be demonstrated invitro by methods known to the person skilled in the art, such as, for example, inhibitory halo tests or plate-diffusion tests.

A compound of the general formula I is effective against Gram-positive bacteria, e.g. *Bacillus subtilis* ATCC 6633 and *Saphylococcus aureus*, as well as against yeasts, e.g. *Klyveromyces marxianus* or filamentous fungi, e.g. *Glomerella cingulata*, as well as against Gram-negative bacteria, e.g. *Klebsiella pneumoniae*.

The minimal inhibitory concentration is within the range from >0.05 to <20 µg/punched hole.

A nematocidal effect can likewise be demonstrated by an in-vitro test, in which replication and mobility of the nematodes is determined. The chrysospermin active peptides are effective against nematodes, e.g. *Caenorhabditis*, in quantities >10 µg/ml.

As a further characteristic, chrysospermins induce the formation of brown pigments in *Phoma sp*. in the agarplate diffusion test when present in concentrations of >10 µg/punched hole.

In addition, the chrysospermins exhibit inhibition of the formation of allophilic or xenophilic antibodies. This provides the possibility of treating hyperacute, acute and chronic rejection reactions of the recipient against the transplanted organ in an effective manner.

The compounds of the formula I and their physiologically tolerated salts are particularly suitable for treating a multiplicity of cancerous disorders. Those types of cancer which are particularly inhibited by these compounds include, for example, leukemia, in particular chronic leukemia of the T-cell and B-cell types, lymph node cancer, e.g. Hodgkin's or non-Hodgkin's lymphoma, carcinomas, sarcomas or skin cancer. The active compounds can either be administered on their own, for example in the form of microcapsules, in mixtures with each other, or in combination with suitable auxiliary and/or carrier substances.

These symptoms, which are known from the state of the art, cannot be observed when humans and animals are treated with the compounds of the formula I. In contrast to the previously known cytotoxic anti-cancer agents, these active compounds do not have the property of impairing the immune system (Bartlett, Int. J. Immunopharmac., 1986, 8: 199 to 204). This consequently opens up novel approaches to tumor therapy, since the body's own defence system is not impaired whereas the growth of tumor cells is prevented.

The invitro proliferation test with cell cultures is used as the test for the efficacy of chemotherapeutic agents.

Owing to their valuable pharmacological properties, chrysospermins are very suitable for use as pharmaceuticals.

A compound according to the invention, or its salts, can in principle be administered as the substance itself. Its use in admixture with suitable auxiliary agents or carrier materials is preferred. In the case of veterinary pharmaceuticals, the customary feedstuff mixtures can be used as carrier materials, as can all pharmacologically tolerated carrier materials and/or auxiliary substances in the case of humans.

Alkali metal, alkaline earth metal and ammonium salts, including those of organic ammonium bases, are examples of suitable physiologically tolerated salts of the compound of the formula I.

The use also relates to pharmaceutical preparations of the chrysospermins.

The pharmaceuticals according to the invention are generally administered orally or parenterally, but rectal use is in principle also possible. Suitable solid or liquid pharmaceutical preparation forms are, for example, granules, powders, tablets, coated tablets, (micro) capsules, suppositories, syrups, emulsions, suspensions, aerosols, drops or injectable solutions in ampoule form, and preparations with protracted release of the active compound, in association with the preparation of which carrier substances and additives and/or adjuvants such as disintegrants, binders, coating agents, swelling agents, glidants, lubricants, flavorants, sweeteners or solubilizers are customarily employed. Frequently used carrier or auxiliary substances which may be mentioned are, for example, magnesium carbonate, titanium dioxide, lactose, mannitol and other sugars, talc, lactalbumin, gelatin, starch, vitamins, cellulose and its derivatives, animal and vegetable oils, polyethylene glycols, and solvents, such as, for example, sterile water, alcohols, glycerol and polyhydric alcohols.

In addition, a compound according to the invention can be given in combination with further active compounds which have an identical or related mode of action. In the case of rejection reactions, for example, these are antiuricopathic agents, inhibitors of blood platelet aggregation, analgesics and steroidal or nonsteroidal antiinflammatory agents.

Where appropriate, the dosage units for oral administration can be microencapsulated, in order to delay release or to extend it over a relatively long period of time, for example by coating or by embedding the active compound in particulate form in suitable polymers, waxes or the like.

Preferably, the pharmaceutical preparations are produced and administered in dosage units such that each unit contains, as the active constituent, a specified dose of the chrysospermins. In the case of solid dosage units, such as tablets, capsules and suppositories, this dose can amount to up to about 200 mg, preferably, however, about 0.1 to 100 mg, per day, and, in the case of injection solutions in ampoule form, up to about 200 mg, preferably, however, about 0.5 to 100 mg, per day.

The daily dose to be administered depends on the body weight, age, sex and condition of the mammalian subject. However, higher or lower daily doses may sometimes be appropriate. The daily dose may be administered either uniquely in the form of a single dosage unit or else in several smaller dosage units or by the repeated administration of subdivided doses at predetermined intervals.

Finally, in association with the production of the abovementioned pharmaceutical preparation forms, the peptides of the formula I and/or at least one of their physiologically tolerated salts can also be formulated together with other suitable preparation forms and together with other suitable active compounds, for example other antitumor agents, immunoglobulins, monoclonal antibodies, immunostimulatory agents or antibiotics. These compounds can also be administered as an accompaniment to radiation therapy.

The pharmaceuticals according to the invention are produced by bringing one or more compounds of the formula I into the and/or a suitable form for administration using customary carrier substances and, where appropriate, additives and/or auxiliary substances.

EMBODIMENT EXAMPLES

The invention will now be illustrated in more detail by means of the following embodiment examples.

1. a) Preparation of a sporulated mycelium of the strain *Apiocrea chrysosperma* DSM 7444

In order to prepare a sporulated mycelium, *Apiocrea chrysosperma* DSM 7444 is incubated at 25° C. for 15 days on nutrient bases (4% malt extract, 0.4% yeast extract, 1.5% agar sterilization at 110° C. for 35 min; pH 6.0).

b) Preparation of an emersed (surface) stationary culture or preculture of *Apiocrea chrysosperma* DSM 7444 in Erlenmeyer flasks In order to set up emersed stationary cultures, agar pieces from the agar culture mentioned in Example 1a, each of which is 2 cm² in size and overgrown with mycelium, are inoculated into 500 ml Erlenmeyer flasks each of which contains 100 ml of liquid nutrient medium. The nutrient medium has the following composition (g/l): malt extract, 20 glucose, 10; yeast extract, 2; $(NH_4)_2HPO_4$, 5; distilled water, pH 6.0 (sterilization at 110° C. for 25 min). After incubating for 15 days at 28° C., the content of chrysospermins in the stationary culture has reached its maximal value.

c) Preparation of submerged shaken cultures of *Apiocrea chrysosperma* DSM 7444

Cultures set up in 500 ml Erleumeyer flasks as in Examples 1a and 1b are shaken in a shaking incubator at 28° C. and 90 revolutions/min for 5 days. 5 ml of each of these precultures is used for inoculating the main culture. This is effected, once again, in 500 ml Erlenmeyer flasks containing 100 ml of malt extract medium, as described under Example 1b, by fermenting at 28° C. and at 90 revolutions/min for 7 days in a shaking incubator.

2. Preparation and purification of the chrysospermin active peptides 15-day old 5 l stationary cultures are stirred, in each case overnight, with 3×1 l of ethyl acetate the combined ethyl acetate extracts are dried over sodium sulfate and concentrated down to a volume of 50 ml. The major portion of the chrysospermins is subsequently precipitated out by adding 500 ml of n-hexane. The precipitate (about 750 mg) which has formed after the mixture has been left to stand at 4° C. overnight is purified by column chromatography on silica gel 60 (pore diameter: 0.01 to 0.02 mm) using chloroform and chloroform/methanol (8:2; v/v) sequentially. The fractions containing chrysospermins are identified by their inhibitory effect on *Bacillus subtilis* ATCC 6633 and by the fact that they are characteristically stained red on a thin layer chromatogram by a solution of 2% vanillin in conc. sulfuric acid. Yield: 250 mg. Further purification can be effected by repeating the column chromatography on silica gel 60 and by chromatography on Sephadex LH-20 (using methanol as the eluent).

3. Chromatographic fractionation of the chrysospermins

Further purification, and fractionation of the chrysospermins into the individual components A and B as well as C and D, and into the individual components A to D, is effected by repeated preparative high performance liquid chromatography using silica gel RP 18 as the carrier material and acetonitrile/water mixtures as eluents. 10 mg of the product obtained in accordance with Example 2 are dissolved in 1 ml of methanol and loaded on an RP18 HPLC column (250×20 mm ID). Elution is carried out isocratically using acetonitrile/water (50:50 v/v) at a flow rate of 25 ml/min. The separated components are detected at 220 run.

In the first separatory phase, the constituent complexes A+B (retention time 20 min) and C+D (retention time 30 min) are obtained. The eluates, which are collected separately, are concentrated down to the aqueous phase on a rotary evaporator and then lyophilized.

12 mg of chrysospermin A+B and 58 mg of chrysospermin C+D are obtained from 100 mg of crude product employed.

Further fractionation into the components A to D is achieved by renewed preparative HPLC of the constituent complexes A+B and C+D under the conditions given above.

4. Physicochemical properties of the chrysospermins

Appearance: colorless crystalline substance

Chromatographic behavior (TLC, silica gel-aluminum foil Merck): $R_f$ 0.3 to 0.4 (chloroform/methanol 7:3)

Staining by chromatographic detection reagents: 2% vanillin/conc. sulfuric acid: carmine red staining Ninhydrin: weak staining Amino acids in the hydrolysate: Ala, Aib, Leu, Gly, Glu, Pro, Ser, Phe and two further components (Iva, Trp-ol) (detection by GC-MS)

FAB-MS: Mol peaks m/z 1897 (M+ +H+); 1911 (M+ +H+), 1925 (M+ +H+).

5. Influence of substances on the mitogen-induced proliferation of spleen lymphocytes The following abbreviations are used:
AV=Average value
Units=Units
SD=Standard deviation
Con A=concanavalin A
LPS=Lipopolysaccharide
PWM=Pokeweed mitogen
SI=Stimulation index
Chryso=Chrysospermin
SS=Stock solution Basic medium
Click's medium/RPMI 1640 medium (50:50) containing L-glutamine without $NaHCO_3$ in powder form for 10 l (Seromed, Biochrom, Berlin, FRG) is dissolved in 9 l of doubly distilled water and filtered sterile in 900 ml volume bottles.

Washing medium
900 ml of basic medium are buffered with 9.5 ml of 7.5% strength sodium hydrogen carbonate solution and 5 ml of HEPES (N-2-hydroxyethylpiperazine-N-2-ethanesulfonic acid) (Gibco, Eggenstein, FRG).

Working medium
900 ml of basic medium plus 19 ml of $NaHCO_3$ solution (7.5%; 10 ml of HEPES solution and 10 ml of L-glutamine solution (200 mM)).

Medium for the mitogen-induced proliferation of lymphocytes:
Working medium is charged with 1% of heat-inactivated (56° C., 30 min) fetal calf serum (FCS).

Isolation and processing of the spleen cells for the mitogen-induced proliferation of lymphocytes The mice are killed by cervical dislocation and the spleens are removed under sterile conditions. The spleens are cut up on a sterile sieve having a mesh grade of 80 and are strained carefully into a Petri dish containing working medium using the piston of a plastic syringe (10 ml). To remove the erythrocytes from the spleen cell suspension, the mixture is incubated at room temperature for about 1 minute, and with occasional shaking, in hypotonic, 0.17M ammonium chloride solution. Under these conditions, the erythrocytes are lysed, whereas the vitality and reactivity of the lymphocytes are not affected. After centrifugation (7 min/340 g), the lysate is discarded and the cells are washed twice, taken up in the test medium, and adjusted to a cell density of $5 \times 10^6$ cells/ml.

Test sample

The proliferation test is carried out in flatbottomed microtiter plates, the total volume per well being 200 μl.

Formula I and mitogens are dissolved in test medium and diluted to the desired concentration. 50 μl each of formula dilution and mitogen dilution are introduced into the wells (in the test, the values are determined four times) and 100 μl of the spleen cell suspension ($5 \times 10^6$ cells/ml) are added. The mitogens bring about proliferation of different lymphocyte populations and are employed in suboptimal to optimal stimulation concentrations as follows:

(Con A) concavalin A: 0.5—0.25—0.12 μg/ml
(LPS) lipopolysaccharide: 1.0—0.5—0.25 g/ml
(PWM) pokeweed mitogen: 0.5—0.25—0.12% stock solution.

The plates are sealed and incubated at 37° C. and 5% $CO_2$ for 48 h. The degree of proliferation is then determined by radioactively labeling the DNA of dividing cells. For this purpose, 25 μl volumes of tritiated thymidine (from Amersham) having an activity of 0.25 μCi/well (specific activity 29 Ci/mmol) are added to the wells, and the incubation is continued for a further 16 hours.

In order to evaluate the test, the plates are harvested on glass fiber filters using a cell-harvesting appliance (from Skatron), with unincorporated tritiated thymidine being collected in separate waste bottles and only radioactivity which is cellularly bound (in the DNA) being measured. The filters are subsequently dried, sealed in plastic bags and then enclosed in cassettes after the addition of 10 ml of scintillator (from Pharmacia). Measurement takes place in a beta counter (Beta-plate Plate System 1205 from Wallac).

Calculation

Positive control; Spleen lymphocytes with the different mitogens but without the addition of the substance.

Negative control: Spleen lymphocytes in medium (without stimulant) and without addition of the substance.

Negative control for the preparation groups: Spleen lymphocytes in medium (without stimulant) but with the addition of the substance. The % change in proliferation is calculated in comparison with the positive control, the same concentration of the respective mitogen always being used on each occasion.

The stimulation index provides information on the ability of the cells to be stimulated by comparison with the negative control of the respective preparation group.

| Mitogen | Dose | Units | n | AV | SD | SD in % | % change | SI |
|---------|------|-------|---|-----|-----|---------|----------|-----|
| Positive control | | | | | | | | |
| Con A | 0.5 | μg/ml | 4 | 95347 | 7382 | 8 | 0 | 52.1 |
| Con A | 0.25 | μg/ml | 4 | 51945 | 6111 | 12 | 0 | 28.4 |
| Con A | 0.12 | μg/ml | 3 | 18408 | 3777 | 21 | 0 | 10.1 |
| LPS | 1.0 | μg/ml | 4 | 61044 | 2354 | 4 | 0 | 33.4 |
| LPS | 0.5 | μg/ml | 4 | 44816 | 1866 | 4 | 0 | 24.5 |
| LPS | 0.25 | μg/ml | 4 | 30710 | 2205 | 7 | 0 | 16.6 |
| PWM | 0.5 | % SS | 4 | 28193 | 6757 | 24 | 0 | 15.4 |
| PWM | 0.25 | % SS | 4 | 19343 | 3952 | 20 | 0 | 10.5 |
| PWM | 0.12 | % SS | 4 | 17912 | 2073 | 12 | 0 | 9.8 |
| Medium | 0.0 | — | 4 | 1829 | 601 | 33 | 0 | 1.0 |
| CsA 10 μg/ml | | | | | | | | |
| Con A | 0.5 | μg/ml | 4 | 236 | 174 | 74 | −100 | 14.7 |
| Con A | 0.25 | μg/ml | 4 | 229 | 145 | 64 | −100 | 16.4 |
| Con A | 0.12 | μg/ml | 4 | 36 | 10 | 29 | −100 | 2.2 |

-continued

| Mitogen | Dose | Units | n | AV | SD | SD in % | % change | SI |
|---|---|---|---|---|---|---|---|---|
| LPS | 1.0 | µg/ml | 4 | 23 | 2 | 9 | −100 | 1.4 |
| LPS | 0.5 | µg/ml | 4 | 30 | 6 | 19 | −100 | 1.9 |
| LPS | 0.25 | µg/ml | 4 | 19 | 5 | 29 | −100 | 1.2 |
| PWM | 0.5 | % SS | 4 | 29 | 3 | 9 | −100 | 1.8 |
| PWN | 0.25 | % SS | 4 | 24 | 1 | 6 | −100 | 1.5 |
| PWM | 0.12 | % SS | 4 | 33 | 13 | 41 | −100 | 2.1 |
| Medium | 0.0 | — | 4 | 16 | 4 | 23 | −99 | 1.0 |
| | | | | CsA 2 µg/ml | | | | |
| Con A | 0.5 | µg/ml | 4 | 9733 | 373 | 4 | −90 | 28.5 |
| Con A | 0.25 | µg/ml | 4 | 3574 | 367 | 10 | −93 | 10.4 |
| Con A | 0.12 | µg/ml | 4 | 1405 | 127 | 9 | −92 | 4.1 |
| LPS | 1.0 | µg/ml | 3 | 9536 | 1110 | 12 | −84 | 27.9 |
| LPS | 0.5 | µg/ml | 4 | 5274 | 824 | 16 | −88 | 15.4 |
| LPS | 0.25 | µg/ml | 4 | 3080 | 64 | 2 | −90 | 9.0 |
| PWM | 0.5 | % SS | 4 | 2354 | 182 | 8 | −92 | 6.9 |
| PWM | 0.25 | % SS | 4 | 1778 | 55 | 3 | −91 | 5.2 |
| PWM | 0.12 | % SS | 4 | 1478 | 194 | 13 | −92 | 4.3 |
| Medium | 0.0 | — | 4 | 342 | 47 | 14 | −81 | 1.0 |
| | | | | CsA 1 µg/ml | | | | |
| Con A | 0.5 | µg/ml | 4 | 11823 | 507 | 4 | −88 | 29.3 |
| Con A | 0.25 | µg/ml | 4 | 3673 | 652 | 18 | −93 | 9.1 |
| Con A | 0.12 | µg/ml | 4 | 1526 | 101 | 7 | −92 | 3.8 |
| LPS | 1.0 | µg/ml | 4 | 13284 | 1374 | 10 | −78 | 33.0 |
| LPS | 0.5 | µg/ml | 4 | 6982 | 699 | 10 | −84 | 17.3 |
| LPS | 0.25 | µg/ml | 4 | 4832 | 613 | 13 | −84 | 12.0 |
| PWM | 0.5 | % SS | 4 | 2964 | 332 | 11 | −89 | 7.3 |
| PWN | 0.25 | % SS | 4 | 2156 | 78 | 4 | −89 | 5.3 |
| PWM | 0.12 | % SS | 4 | 1925 | 144 | 7 | −89 | 4.8 |
| Medium | 0.0 | — | 4 | 403 | 19 | 5 | −78 | 1.0 |
| | | | | CsA 0.2 µg/ml | | | | |
| Con A | 0.5 | µg/ml | 4 | 18370 | 579 | 3 | −81 | 35.5 |
| Con A | 0.25 | µg/ml | 4 | 5766 | 386 | 7 | −89 | 11.3 |
| Con A | 0.12 | µg/ml | 4 | 2010 | 80 | 4 | −89 | 3.9 |
| LPS | 1.0 | µg/ml | 4 | 23773 | 4940 | 21 | −61 | 45.9 |
| LPS | 0.5 | µg/ml | 4 | 16727 | 670 | 4 | −63 | 32.3 |
| LPS | 0.25 | µg/ml | 4 | 10136 | 336 | 3 | −67 | 19.6 |
| PWM | 0.5 | % SS | 4 | 3928 | 306 | 8 | −86 | 7.6 |
| PWM | 0.25 | % SS | 4 | 3085 | 257 | 8 | −84 | 6.0 |
| PWM | 0.12 | % SS | 4 | 2430 | 270 | 11 | −86 | 4.7 |
| Medium | 0.0 | — | 4 | 518 | 48 | 9 | −72 | 1.0 |
| | | | | CsA 0.1 µg/ml | | | | |
| Con A | 0.5 | µg/ml | 4 | 20737 | 1584 | 8 | −78 | 3.7 |
| Con A | 0.25 | µg/ml | 4 | 5711 | 465 | 8 | −89 | 10.4 |
| Con A | 0.12 | µg/ml | 4 | 1938 | 213 | 11 | −89 | 3.5 |
| LPS | 1.0 | µg/ml | 4 | 29219 | 1486 | 5 | −52 | 53.1 |
| LPS | 0.5 | µg/ml | 4 | 18066 | 1086 | 6 | −60 | 32.8 |
| LPS | 0.25 | µg/ml | 4 | 11171 | 238 | 2 | −64 | 20.3 |
| PWM | 0.5 | % SS | 4 | 4819 | 215 | 4 | −83 | 8.8 |
| PWM | 0.25 | % SS | 4 | 3198 | 183 | 6 | −83 | 5.8 |
| PWM | 0.12 | % SS | 4 | 2575 | 162 | 6 | −86 | 4.7 |
| Medium | 0.0 | — | 4 | 550 | 35 | 6 | −70 | 1.0 |
| | | | | Chryso A/B 10 µg/ml | | | | |
| Con A | 0.5 | µg/ml | 3 | 10830 | 3368 | 31 | −89 | 12.0 |
| Con A | 0.25 | µg/ml | 4 | 12891 | 548 | 4 | −75 | 14.2 |
| Con A | 0.12 | µg/ml | 4 | 8274 | 1192 | 14 | −55 | 9.0 |
| LPS | 1.0 | µg/ml | 3 | 6101 | 457 | 7 | −90 | 6.7 |
| LPS | 0.5 | µg/ml | 4 | 5697 | 231 | 4 | −87 | 6.3 |
| LPS | 0.25 | µg/ml | 4 | 4452 | 719 | 16 | −86 | 4.9 |
| PWM | 0.5 | % SS | 4 | 5090 | 534 | 10 | −82 | 5.6 |
| PWM | 0.25 | % SS | 4 | 5621 | 265 | 5 | −71 | 6.2 |
| PWM | 0.12 | % SS | 3 | 3979 | 686 | 17 | −78 | 4.4 |
| Medium | 0.0 | — | 4 | 905 | 311 | 34 | −50 | 1.0 |
| | | | | Chryso A/B 2 µg/ml | | | | |
| Con A | 0.5 | µg/ml | 4 | 174598 | 2230 | 1 | 83 | 47.1 |
| Con A | 0.25 | µg/ml | 4 | 129118 | 2880 | 2 | 149 | 34.8 |
| Con A | 0.12 | µg/ml | 4 | 62937 | 11224 | 18 | 242 | 17.0 |
| LPS | 1.0 | µg/ml | 4 | 74404 | 1886 | 3 | 22 | 20.1 |
| LPS | 0.5 | µg/ml | 4 | 58285 | 1669 | 3 | 30 | 15.7 |
| LPS | 0.25 | µg/ml | 4 | 47409 | 3056 | 6 | 54 | 12.8 |
| PWM | 0.5 | % SS | 4 | 51533 | 3863 | 7 | 83 | 13.9 |
| PWM | 0.25 | % SS | 4 | 43847 | 1837 | 4 | 127 | 11.8 |
| PWM | 0.12 | % SS | 4 | 32537 | 1237 | 4 | 82 | 8.8 |
| Medium | 0.0 | — | 4 | 3708 | 264 | 7 | 103 | 1.0 |
| | | | | Chryso A/B 1 µg/ml | | | | |
| Con A | 0.5 | µg/ml | 4 | 150893 | 6464 | 4 | 58 | 36.7 |
| Con A | 0.25 | µg/ml | 4 | 119556 | 1975 | 2 | 130 | 29.1 |
| Con A | 0.12 | µg/ml | 4 | 60761 | 3799 | 6 | 230 | 14.8 |
| LPS | 1.0 | µg/ml | 4 | 61155 | 8047 | 13 | 0 | 14.9 |
| LPS | 0.5 | µg/ml | 4 | 54958 | 2463 | 4 | 23 | 13.4 |

-continued

| Mitogen | Dose | Units | n | AV | SD | SD in % | % change | SI |
|---|---|---|---|---|---|---|---|---|
| LPS | 0.25 | μg/ml | 4 | 44582 | 1861 | 4 | 45 | 10.8 |
| PWM | 0.5 | % SS | 4 | 53906 | 3318 | 6 | 91 | 13.1 |
| PWM | 0.25 | % SS | 4 | 42879 | 1725 | 4 | 122 | 10.4 |
| PWM | 0.12 | % SS | 4 | 31055 | 1013 | 3 | 73 | 7.5 |
| Medium | 0.0 | — | 4 | 4114 | 485 | 12 | 125 | 1.0 |
| Chryso A/B 0.2 μg/ml | | | | | | | | |
| Con A | 0.5 | μg/ml | 4 | 168295 | 4045 | 2 | 77 | 50.4 |
| Con A | 0.25 | μg/ml | 4 | 124940 | 3446 | 3 | 141 | 37.4 |
| Con A | 0.12 | μg/ml | 4 | 67198 | 8378 | 12 | 265 | 20.1 |
| LPS | 1.0 | μg/ml | 4 | 70965 | 4476 | 6 | 16 | 21.2 |
| LPS | 0.5 | μg/ml | 4 | 59873 | 1326 | 2 | 34 | 17.9 |
| LPS | 0.25 | μg/ml | 4 | 44695 | 660 | 1 | 46 | 13.4 |
| PWM | 0.5 | % SS | 4 | 49539 | 1364 | 3 | 76 | 14.8 |
| PWM | 0.25 | % SS | 4 | 41145 | 1357 | 3 | 113 | 12.3 |
| PWM | 0.12 | % SS | 4 | 31056 | 1722 | 6 | 73 | 9.3 |
| Medium | 0.0 | — | 4 | 3338 | 280 | 8 | 83 | 1.0 |
| Chryso A/B 0.1 μg/ml | | | | | | | | |
| Con A | 0.5 | μg/ml | 4 | 167376 | 6191 | 4 | 76 | 44.7 |
| Con A | 0.25 | μg/ml | 4 | 134097 | 6943 | 5 | 158 | 35.8 |
| Con A | 0.12 | μg/ml | 4 | 62049 | 2175 | 4 | 237 | 16.5 |
| LPS | 1.0 | μg/ml | 4 | 68121 | 8000 | 12 | 12 | 18.2 |
| LPS | 0.5 | μg/ml | 4 | 61682 | 2884 | 5 | 38 | 16.5 |
| LPS | 0.25 | μg/ml | 4 | 44654 | 1859 | 4 | 45 | 11.9 |
| PWM | 0.5 | % SS | 4 | 52551 | 1348 | 3 | 86 | 14.0 |
| PWM | 0.25 | % SS | 4 | 41341 | 473 | 1 | 114 | 11.0 |
| PWM | 0.12 | % SS | 4 | 30586 | 219 | 1 | 71 | 8.2 |
| Medium | 0.0 | — | 4 | 3747 | 354 | 9 | 105 | 1.0 |
| Chryso C/D 10 μg/ml | | | | | | | | |
| Con A | 0.5 | μg/ml | 4 | 219 | 29 | 13 | −100 | 4.7 |
| Con A | 0.25 | μg/ml | 4 | 171 | 35 | 20 | −100 | 3.7 |
| Con A | 0.12 | μg/ml | 4 | 85 | 13 | 15 | −100 | 1.8 |
| LPS | 1.0 | μg/ml | 4 | 47 | 4 | 8 | −100 | 1.0 |
| LPS | 0.5 | μg/ml | 4 | 100 | 37 | 37 | −100 | 2.2 |
| LPS | 0.25 | μg/ml | 4 | 66 | 20 | 30 | −100 | 1.4 |
| PWM | 0.5 | % SS | 4 | 87 | 17 | 19 | −100 | 1.9 |
| PWM | 0.25 | % SS | 4 | 61 | 4 | 7 | −100 | 1.3 |
| PWM | 0.12 | % SS | 4 | 67 | 14 | 21 | −100 | 1.5 |
| Medium | 0.0 | — | 4 | 46 | 12 | 25 | −98 | 1.0 |
| Chryso C/D 2 μg/ml | | | | | | | | |
| Con A | 0.5 | μg/ml | 4 | 168994 | 2499 | 1 | 77 | 46.1 |
| Con A | 0.25 | μg/ml | 4 | 127101 | 3894 | 3 | 145 | 34.7 |
| Con A | 0.12 | μg/ml | 4 | 55318 | 1539 | 3 | 201 | 15.1 |
| LPS | 1.0 | μg/ml | 3 | 46853 | 1529 | 3 | −23 | 12.8 |
| LPS | 0.5 | μg/ml | 4 | 34354 | 892 | 3 | −23 | 9.4 |
| LPS | 0.25 | μg/ml | 4 | 26359 | 1482 | 6 | −14 | 7.2 |
| PWM | 0.5 | % SS | 4 | 31481 | 815 | 3 | 12 | 8.6 |
| PWM | 0.25 | % SS | 4 | 26621 | 3468 | 13 | 38 | 7.3 |
| PWM | 0.12 | % SS | 4 | 19632 | 690 | 4 | 10 | 5.4 |
| Medium | 0.0 | — | 4 | 3663 | 319 | 9 | 100 | 1.0 |
| Chryso C/D 1 μg/ml | | | | | | | | |
| Con A | 0.5 | μg/ml | 4 | 186499 | 5377 | 3 | 96 | 46.8 |
| Con A | 0.25 | μg/ml | 4 | 131375 | 1171 | 1 | 153 | 33.0 |
| Con A | 0.12 | μg/ml | 4 | 62219 | 4252 | 7 | 238 | 15.6 |
| LPS | 1.0 | μg/ml | 4 | 66784 | 8884 | 13 | 9 | 16.8 |
| LPS | 0.5 | μg/ml | 4 | 52076 | 1741 | 3 | 16 | 13.1 |
| LPS | 0.25 | μg/ml | 4 | 38876 | 1957 | 5 | 27 | 9.8 |
| PWM | 0.5 | % SS | 4 | 57400 | 12906 | 22 | 104 | 14.4 |
| PWM | 0.25 | % SS | 4 | 37675 | 1814 | 5 | 95 | 9.5 |
| PWM | 0.12 | % SS | 4 | 31638 | 2867 | 9 | 77 | 7.9 |
| Medium | 0.0 | — | 4 | 3981 | 462 | 12 | 118 | 1.0 |
| Chryso C/D 0.2 μg/ml | | | | | | | | |
| Con A | 0.5 | μg/ml | 4 | 174176 | 1882 | 1 | 83 | 37.9 |
| Con A | 0.25 | μg/ml | 4 | 131338 | 3245 | 2 | 153 | 28.6 |
| Con A | 0.12 | μg/ml | 4 | 62224 | 3767 | 6 | 238 | 13.5 |
| LPS | 1.0 | μg/ml | 4 | 67510 | 8444 | 13 | 11 | 14.7 |
| LPS | 0.5 | μg/ml | 4 | 58617 | 1115 | 2 | 31 | 12.8 |
| LPS | 0.25 | μg/ml | 4 | 47545 | 1183 | 2 | 55 | 10.3 |
| PWM | 0.5 | % SS | 4 | 56805 | 2137 | 4 | 101 | 12.3 |
| PWM | 0.25 | % SS | 4 | 43419 | 1990 | 5 | 124 | 9.4 |
| PWM | 0.12 | % SS | 4 | 30425 | 2844 | 9 | 70 | 6.6 |
| Medium | 0.0 | — | 4 | 4596 | 188 | 4 | 151 | 1.0 |
| Chryso C/D 0.1 μg/ml | | | | | | | | |
| Con A | 0.5 | μg/ml | 4 | 174085 | 1944 | 1 | 83 | 40.5 |
| Con A | 0.25 | μg/ml | 4 | 122841 | 1477 | 1 | 136 | 28.6 |
| Con A | 0.12 | μg/ml | 4 | 61752 | 5629 | 9 | 235 | 14.4 |
| LPS | 1.0 | μg/ml | 4 | 70069 | 2049 | 3 | 15 | 16.3 |
| LPS | 0.5 | μg/ml | 4 | 59291 | 3267 | 6 | 32 | 13.8 |
| LPS | 0.25 | μg/ml | 4 | 42247 | 1788 | 4 | 38 | 9.8 |
| PWM | 0.5 | % SS | 4 | 55930 | 2910 | 5 | 98 | 13.0 |

| Mitogen | Dose | Units | n | AV | SD | SD in % | % change | SI |
|---|---|---|---|---|---|---|---|---|
| PWM | 0.25 | % SS | 4 | 47362 | 1848 | 4 | 145 | 11.0 |
| PWM | 0.12 | % SS | 4 | 30606 | 5959 | 19 | 71 | 7.1 |
| Medium | 0.0 | — | 4 | 4295 | 271 | 6 | 135 | 1.0 |

6. Tumor cell proliferation (in vitro):

The proliferation test is carried out in round-bottomed microtiter plates. Tumor cells, originally obtained from the American Type Culture Collection (ATCC), are grown in a permanent stock holding in serum-free medium (CG medium from Vitromex) and are used for the test in their logarithmic phase of growth. The following tumor cell lines are used routinely:

1) A 20.2 J = plasmacytoma
2) 20−10−5S = hybridoma
3) EL4 = T-helper cell lymphoma
4) K562 = undifferentiated myelomonocytic line The cells are adjusted in serum-free CG medium to a cell density of $4 \times 10^4$ cells/ml and 100 μl are pipetted into each well. Formula I is dissolved in CG medium and diluted down to the desired concentration, and 100 μl are added to the cells (total volume, 200 μl containing $4 \times 10^3$ cells). The respective values are also ascertained by 4-fold determination.

After incubating for 48 hours, the proliferation of the cells is ascertained by the incorporation of radioactive tritiated thymidine in analogy with the procedure described under number 5.

Calculation

Positive control: Cells of each cell line are incubated in medium = normal proliferation % Changes in proliferation of the individual preparation concentrations are calculated by comparison with the positive control.

| Preparation | μg/ml | n | AV | SD | SD in % | % Change |
|---|---|---|---|---|---|---|
| Cell line: EL 4 | | | | | | |
| Cyclosporin A | 10.000 | 4 | 17 | 5 | 29 | −100 |
| | 5.000 | 4 | 14 | 1 | 9 | −100 |
| | 2.500 | 4 | 22 | 8 | 35 | −100 |
| | 1.000 | 4 | 30 | 6 | 21 | −100 |
| | 0.500 | 4 | 2608 | 409 | 16 | −97 |
| | 0.100 | 4 | 27333 | 1725 | 6 | −73 |
| Chrysospermin A/B | 10.000 | 4 | 27 | 23 | 85 | −100 |
| | 5.000 | 4 | 65835 | 4013 | 6 | −35 |
| | 2.500 | 4 | 87715 | 3042 | 3 | −14 |
| | 1.000 | 4 | 90812 | 2784 | 3 | −11 |
| | 0.500 | 4 | 92122 | 5037 | 5 | −10 |
| | 0.100 | 4 | 93904 | 4574 | 5 | −8 |
| Chrysospermin C/D | 10.000 | 4 | 22 | 4 | 17 | −100 |
| | 5.000 | 4 | 25 | 9 | 35 | −100 |
| | 2.500 | 4 | 72404 | 3527 | 5 | −29 |
| | 1.000 | 4 | 90971 | 2212 | 2 | −11 |
| | 0.500 | 4 | 90831 | 574 | 1 | −11 |
| | 0.100 | 4 | 91906 | 4771 | 5 | −10 |
| Cell line: K 562 | | | | | | |
| Cyclosporin A | 10.000 | 4 | 33 | 6 | 17 | −100 |
| | 5.000 | 4 | 1027 | 67 | 7 | −99 |
| | 2.500 | 4 | 19191 | 978 | 5 | −85 |
| | 1.000 | 4 | 83706 | 4384 | 5 | −36 |
| | 0.500 | 4 | 100838 | 5169 | 5 | −23 |
| | 0.100 | 4 | 126497 | 6596 | 5 | −4 |
| Chrysospermin A/B | 10.000 | 4 | 1560 | 403 | 26 | −99 |
| | 5.000 | 4 | 18441 | 1733 | 9 | −86 |
| | 2.500 | 4 | 52008 | 1459 | 3 | −60 |
| | 1.000 | 4 | 123531 | 2903 | 2 | −6 |
| | 0.500 | 4 | 124321 | 5204 | 4 | −5 |
| | 0.100 | 4 | 130717 | 6127 | 5 | −1 |
| Chrysospermin | 10.000 | 4 | 19 | 3 | 18 | −100 |
| C/D | 5.000 | 4 | 1143 | 265 | 23 | −99 |
| | 2.500 | 4 | 16716 | 1384 | 8 | −87 |
| | 1.000 | 4 | 112024 | 8598 | 8 | −15 |
| | 0.500 | 4 | 124858 | 2260 | 2 | −5 |
| | 0.100 | 4 | 130525 | 5893 | 5 | −1 |
| CT = 2501 = | | | | | | |
| Cell line: A20.2.J | | | | | | |
| Cyclosporin A | 10.000 | 4 | 17 | 3 | 18 | −100 |
| | 5.000 | 4 | 31 | 9 | 28 | −100 |
| | 2.500 | 4 | 1495 | 436 | 29 | −99 |
| | 1.000 | 4 | 24936 | 1278 | 5 | −85 |
| | 0.500 | 4 | 58911 | 1357 | 2 | −64 |
| | 0.100 | 4 | 136012 | 4587 | 3 | −16 |
| Chrysospermin A/B | 10.000 | 4 | 35 | 9 | 25 | −100 |
| | 5.000 | 4 | 39511 | 3265 | 8 | −76 |
| | 2.500 | 4 | 148134 | 5418 | 4 | −8 |
| | 1.000 | 4 | 156242 | 4857 | 3 | −3 |
| | 0.500 | 4 | 157810 | 4028 | 3 | −2 |
| | 0.100 | 4 | 154432 | 6877 | 4 | −5 |
| Chrysospermin C/D | 10.000 | 4 | 31 | 9 | 31 | −100 |
| | 5.000 | 4 | 74 | 41 | 55 | −100 |
| | 2.500 | 4 | 80974 | 2016 | 2 | −50 |
| | 1.000 | 4 | 160019 | 5467 | 3 | −1 |
| | 0.500 | 4 | 156971 | 8541 | 5 | −3 |
| | 0.100 | 4 | 152791 | 8817 | 6 | −6 |
| Cell line: 20-10-5S | | | | | | |
| Cyclosporin A | 10.000 | 4 | 20 | 5 | 28 | −100 |
| | 5.000 | 4 | 58 | 51 | 88 | −100 |
| | 2.500 | 4 | 19 | 10 | 54 | −100 |
| | 1.000 | 4 | 44 | 46 | 105 | −100 |
| | 0.500 | 4 | 29 | 17 | 57 | −100 |
| | 0.100 | 4 | 33784 | 5010 | 15 | −42 |
| Chrysospermin A/B | 10.000 | 4 | 16 | 5 | 29 | −100 |
| | 5.000 | 4 | 20865 | 5059 | 24 | −64 |
| | 2.500 | 4 | 62699 | 6069 | 10 | +8 |
| | 1.000 | 4 | 62344 | 2851 | 5 | +7 |
| | 0.500 | 4 | 60208 | 1632 | 3 | +4 |
| | 0.100 | 4 | 65147 | 2830 | 4 | +12 |
| Chrysospermin C/D | 10.000 | 4 | 16 | 3 | 20 | −100 |
| | 5.000 | 4 | 28 | 19 | 67 | −100 |
| | 2.500 | 4 | 47995 | 1248 | 3 | −17 |
| | 1.000 | 4 | 60538 | 1657 | 3 | 4 |
| | 0.500 | 4 | 61930 | 4507 | 7 | 7 |
| | 0.100 | 4 | 59966 | 1819 | 3 | 3 |

7. Influence of CSA and chrysospermin A/B and C/D on the production of interleukin 2/3

The method for isolating the lymphocytes is described under point 5. Mixture for isolating interleukin: Macroplates possessing in each case 12 wells: $5 \times 10^6$ NMRI spleen cells in 4 ml of CTL medium (= cytotoxic T-lymphocyte medium) + 2 μl/ml concanavalin A or without stimulant and CSA (cyclosporin A), chrysospermin A/B or C/D in various concentrations. 24 h stimulation: supernatant is isolated cell-free.

Cytotox. T-lymphocyte CIR medium (from Biochrom) medium: +5% fetal calf serum +1% NEA (= nonessential amino acids) +1% pyruvate + ME (β-mercaptoethanol $5 \times 10^{-5}$ ml); all from Gibco This supernatant is added to cell lines which are growing independently of interleukin 2/3 and the content of interleukin is measured from the proliferation.

CTLL cells→IL-2 detection
DA 1 cells→IL-3 detection

Mixture for testing the content of interleukin in the supernatant:

$4 \times 10^3$ of the abovementioned cells/100 μl + 100 μl of supernatant=50%} + 50 μl of supernatant=25%} total volume 200 μl per well + 25 μl of supernatant=12.5%} + 12.5 μl of supernatant=6.25%}

The plates are incubated for 48 hours and proliferation of the cells is ascertained by incorporation of radioactive tritiated thymidine in analogy with the procedure described under point 5.

Calculation

Spleen cells produce interleukin 2 and 3 without the substance and with concanavalin A as the stimulant. This supernatant is used as the positive reference control, and the respective dilutions of the supernatants of the individual preparation concentrations are compared with it.

Calculation for significance using $p \leqq 0.5$.

Internal test standard: To check the magnitude of the content of interleukin 2 and 3 in the individual groups, interleukin 2 and interleukin 3 of known concentrations are included in the test as controls.

Microscopic assessment after 20 h. 50 μg/ml and 20 μg/ml of all 3 substances 100% dead cells

| | Interleukin 2 control: | | |
|---|---|---|---|
| | | | Counts |
| (1) | 80 μg/ml | 200 U/ml | 233,430 |
| (2) | 40 μg/ml | 100 U/ml | 229,583 |
| (3) | 20 μg/ml | 50 U/ml | 230,215 |
| (4) | 10 μg/ml | 25 U/ml | 225,827 |
| (5) | 5 μg/ml | 12.5 U/ml | 183,303 |
| (6) | 2.5 μg/ml | 6.25 U/ml | 78,836 |
| (7) | 1.25 μg/ml | 3.125 U/ml | 42,751 |
| (8) | Medium | Medium | 43 |

| | Interleukin 3 control: | |
|---|---|---|
| (1) | 20% | 44,525 |
| (2) | 10% | 38,252 |
| (3) | 5% | 33,018 |
| (4) | 2.5% | 24,826 |
| (5) | 1.25% | 12,102 |
| (6) | 0.6 · 125% | 5,305 |
| (7) | 0.3 · 2% | 2,580 |
| (8) | Medium | 20 |

| | Control | 50 μg/ml | 20 μg/ml | 10 μg/ml | 2 μg/ml | 0.2 μg/ml |
|---|---|---|---|---|---|---|
| | | Interleukin 3 | | | | |
| | | Cyclosporin A | | | | |
| 50% | 9798 | ∅ | ∅ | ∅ | ∅ | ∅ |
| 25% | 4300 | ∅ | ∅ | ∅ | ∅ | ∅ |
| 12.5% | 1218 | ∅ | ∅ | ∅ | ∅ | ∅ |
| 6.25% | 181 | ∅ | ∅ | ∅ | ∅ | ∅ |
| Chrysospermin A/B | | | | | | |
| 50% | 9798 | ∅ | ∅ | 9864 | 15671* 11.0 | 14766 * |
| | | | | | 59.8 | |
| 25% | 4300 | ∅ | ∅ | 3468 | 5969 * | 5568 * |
| 12.5% | 1218 | ∅ | ∅ | 685 | 2403 * | 2165 * |
| 6.25% | 181 | ∅ | ∅ | 42 | 515 * | 498 * |
| C/D | | | | | | |
| 50% | 9798 | ∅ | ∅ | 321 | 15121 * | 15613 * |
| 25% | 4300 | ∅ | ∅ | ∅ | 5907 * | 5817 * |
| 12.5% | 1218 | ∅ | ∅ | ∅ | 2170 * | 1863 * |
| 6.25% | 181 | ∅ | ∅ | ∅ | 519 * | 292 * |
| | | Interleukin 2 | | | | |
| CSA | | | | | | |
| 50% | 73812 | 2090 | 162 | ∅ | ∅ | ∅ |
| 25% | 30347 | 982 | 153 | ∅ | ∅ | ∅ |
| 12.5% | 2766 | ∅ | ∅ | ∅ | ∅ | ∅ |
| 6.25% | 270 | ∅ | ∅ | ∅ | ∅ | ∅ |
| A/B | | | | | | |
| 50% | 73812 | ∅ | 3663 | 70918 | 85632 | 83622 |
| 25% | 30347 | ∅ | 796 | 45892 * | 42054 * | 72513 * |
| 12.5% | 2766 | ∅ | 693 | 13617 * | 5821 * | 9610 * |
| 6.25% | 270 | ∅ | ∅ | 458 | 347 | 419 |
| C/D | | | | | | |
| 50% | 73812 | ∅ | ∅ | 19483 | 92026 * | 81028 |
| 25% | 30347 | ∅ | ∅ | 11524 | 53193 * | 52904 * |
| 12.5% | 2766 | ∅ | ∅ | 696 | 8812 * | 19025 * |
| 6.25% | 170 | ∅ | ∅ | 165 | 614 | 4514 * |

8. Chemiluminescence invitro

Teflon pouch cultivation method: Both the femurs are removed under sterile conditions from 6–10 week-old NMRI mice in such a way that they are as free of muscle as possible. The bone marrow is flushed out with 10 ml of working medium (see point 5) by inserting a cannula on one side of the bone, and dispersed into individual cells by repeatedly drawing it up into the syringe.

Teflon foil (Biofolie 25, from Heraeus) is welded into the form of pouches of the size 5 cm×30 cm with the hydrophilic side directed inwards and then steam-sterilized at 121° C. and 1.1 bar for 20 minutes. 4×10⁶ stock cells in 60 ml of working medium (see point 5) containing 20% FCS and 30% L929 supernatant (as the source of colony stimulating factor 1 CSF1 for the differentiation into macrophages) are added to these sterile pouches, which are then incubated at 37° C. and 5% $CO_2$ for 8 days.

The teflon pouch method enables macrophages to be raised from an NMRI mouse. The cells are given 8 days to differentiate. Subsequently they are stained with Giemsa stain in order to be able to determine the number of macrophages.

Mixture

200 μl of substance at the respective concentration
350 μl of RPMI medium 1640 (Biochrom) without phenol red
100 μl of luminol (200 μM)
100 μl of macrophages (2.5×10⁶/ml)
250 μl of PMA (3.5 μM=Phorbol myristate acetate)

1000 μl ≈ PMA, 0.875 μM  
≈ Luminol, 20 μM  
are incubated with 2.5 × 10⁶ macrophages Chemiluminescence is measured in a Picolite 6500 (from Packard, USA); photons per 10 seconds.

The macrophages are activated by the addition of PMA. 2 mixtures per preparation concentration (results=X=average values)

Without preincubation: Test substance+PMA and measure subsequently 1 h. Preincubation: Test substance at 37° C. for 1 h., then PMA and measure subsequently

| Minutes | Without preincubation Positive control | 1 h. Preincubation Positive control |
|---|---|---|
| 0' | 23835 | 34360 |
| 2' | 92600 | 95605 |
| 4' | 74465 | 74940 |
| 6' | 66300 | 55480 |
| 8' | 57955 | 47450 |
| 10' | 51580 | 42210 |
| 12' | 45850 | 36795 |
| 14' | 39460 | 32745 |
| 16' | 35065 | 30050 |
| 18' | 33790 | 29225 |

| | Without preincubation | | | 1. Preincubation | | |
|---|---|---|---|---|---|---|
| Minutes | CsA 50 μg/ml | A/B 50 μg/ml | C/D 50 μg/ml | CsA 50 μg/ml | A/B 50 μg/ml | C/D 50 μg/ml |
| 0' | 16425 | 14910 | 16155 | 14680 | 18405 | 22425 |
| 2' | 13869 | 45610 | 25090 | 14405 | 42450 | 30470 |
| 4' | 15784 | 29505 | 22215 | 18630 | 27295 | 21060 |
| 6' | 21995 | 24615 | 21090 | 21315 | 23805 | 18330 |
| 8' | 23950 | 22760 | 22085 | 21715 | 21115 | 17660 |
| 10' | 24820 | 20460 | 22175 | 21345 | 18530 | 17610 |
| 12' | 23425 | 17564 | 21035 | 20455 | 17715 | 17600 |
| 14' | 22400 | 17505 | 20070 | 20335 | 17985 | 16965 |
| 16' | 22625 | 15169 | 18255 | 21340 | 16245 | 17080 |
| 18' | 21930 | 13835 | 17309 | 21055 | 15835 | 15765 |

| | Without preincubation | | | 1 h. Preincubation | | |
|---|---|---|---|---|---|---|
| | CsA | A/B | C/D | CsA | A/B | C/D |
| Minutes | 10 μg/ml | 10 μg/ml | 10 μg/ml | 10 μg/ml | 10 μg/ml | 10 μg/ml |
| 0' | 11051 | 31205 | 27095 | 10960 | 46290 | 44245 |
| 2' | 17060 | 111849 | 97595 | 15675 | 129315 | 124995 |
| 4' | 36365 | 81980 | 76105 | 37100 | 84195 | 89300 |
| 6' | 30455 | 77230 | 69970 | 30080 | 72935 | 77950 |
| 8' | 29755 | 70430 | 64035 | 26065 | 62390 | 73230 |
| 10' | 28555 | 66800 | 64465 | 25060 | 57820 | 70070 |
| 12' | 27960 | 61285 | 61940 | 24075 | 52245 | 69655 |
| 14' | 26665 | 56980 | 59810 | 46040 | 47335 | 63110 |
| 16' | 25605 | 515151 | 58130 | 41630 | 43650 | 59310 |
| 18' | 24175 | 46940 | 54050 | 20990 | 42065 | 56880 |

| | Without preincubation | | | 1 h. Preincubation | | |
|---|---|---|---|---|---|---|
| | CsA | A/B | C/D | CsA | A/B | C/D |
| Minutes | 5 μg/ml | 5 μg/ml | 5 μg/ml | 5 μg/ml | 5 μg/ml | 5 μg/ml |
| 0' | 13755 | 22210 | 24520 | 10270 | 53265 | 38675 |
| 2' | 35215 | 106665 | 105205 | 26905 | 131975 | 120450 |
| 4' | 43660 | 77080 | 76620 | 44155 | 97245 | 90695 |
| 6' | 37095 | 72010 | 75345 | 34020 | 83945 | 79420 |
| 8' | 35505 | 69565 | 70915 | 29475 | 77030 | 74430 |
| 10' | 33465 | 67640 | 68440 | 28080 | 69515 | 72315 |
| 12' | 30935 | 62835 | 67550 | 25685 | 64360 | 65520 |
| 14' | 29235 | 58885 | 65280 | 23775 | 57995 | 63277 |
| 16' | 27800 | 55405 | 58435 | 22855 | 56035 | 59030 |
| 18' | 25775 | 52860 | 54015 | 21225 | 52560 | 57400 |

| | Without preincubation | | | 1 h. Preincubation | | |
|---|---|---|---|---|---|---|
| | CsA | A/B | C/D | CsA | A/B | C/D |
| Minutes | 1 μg/ml | 1 μg/ml | 1 μg/ml | 1 μg/ml | 1 μg/ml | 1 μg/ml |
| 0' | 12100 | 16595 | 19710 | 24570 | 16550 | 23400 |
| 2' | 60880 | 948255 | 97040 | 75020 | 110160 | 113455 |
| 4' | 47915 | 69665 | 71185 | 59415 | 75800 | 76945 |
| 6' | 39600 | 64225 | 64900 | 44310 | 61185 | 60380 |
| 8' | 38210 | 61365 | 57805 | 37860 | 58505 | 54930 |
| 10' | 36230 | 58231 | 51410 | 33715 | 55910 | 47705 |
| 12' | 32615 | 54115 | 46950 | 31295 | 51265 | 41055 |
| 14' | 28520 | 49605 | 61420 | 27260 | 46470 | 36430 |
| 16' | 25930 | 44700 | 36790 | 25870 | 44145 | 33485 |
| 18' | 24570 | 39165 | 32015 | 24200 | 40125 | 31520 |

9. MLR one way (mixed lymphocyte reaction) NMRI spleen cells against EL4 tumor cells mitomycin C treatment: (EL4 are no longer able to proliferate)

7.75×10⁶ EL4 cells are incubated with 30 μg of mitomycin C in 2 ml≈(1×10⁶ cells+3.9 μg of mitomycin in 258 μl of medium) at 37° C. for 1 h. in a water bath, and subsequently left to incubate for a further 30 minutes in fresh medium in a water bath. Finally, the cells are washed twice with basic medium.

Mixture

100 μl of NMRI spleen cells 5×10⁵/well
50 μl of EL4 cells (2.3×10⁴) or (4.7×10⁴) per well
50 μl of substance (4×conc.) in CTL medium (CTL medium containing 5% fetal calf serum; 1% NEA; 1% Pyruvate+ME) in flat-bottomed microtiter plates.

Four-fold mixture; 5 days of incubation;
16 h. H³-thymidine incorporation.
Concentrations of the substances:

1 10 μg/ml
2 5 μg/ml
3 1 μg/ml
4 0.5 μg/ml
5 0.1 μg/ml
6 0.05 μg/ml
7 0.01 μg/ml

| | α 2.3 × 10⁴ EL4 Cells | | | | | | α 4.7 × 10⁴ EL4-Zellen | | | | | |
|---|---|---|---|---|---|---|---|---|---|---|---|---|
| | CsA | | A/B | | C/D | | CsA | | A/B | | C/D | |
| μg/ml | cpm | % Inhibition | cpm | % Inhibition | cpm | % Inhibition | cpm | % Inhibition | cpm | % Inhibition | cpm | % Inhibition |
| 10    | 43    | −99.9% | 672   | −99.0% | 38    | −99.9% | 31    | −99.9% | 1024  | −98.4% | 66    | −99.9% |
| 5     | 89    | −99.9% | 18108 | −74.3% | 5507  | −92.2% | 143   | −99.8% | 47392 | −26.7% | 5113  | −92.1% |
| 1     | 848   | −98.8% | 40113 | −43.2% | 53037 | −25.9% | 588   | −89.1% | 46947 | −27.3% | 40940 | −36.6% |
| 0,5   | 1027  | −98.5% | 58355 | −17.3% | 61539 | −12.8% | 1225  | −98.1% | 60116 | −7.0%  | 42461 | −34.3% |
| 0,1   | 2861  | −95.9% | 53836 | −23.7% | 63522 | −10.0% | 2155  | −96.7% | 62910 | −2.6%  | 52197 | −19.2% |
| 0,05  | 3596  | −94.9% | 56839 | −19.5% | 50163 | −28.9% | 4607  | −92.9% | 69001 | +6.8%  | 48498 | −24.9% |
| 0,01  | 22514 | −68.1% | 57942 | −17.9% | 39954 | −43.4% | 24015 | −62.8% | 64675 | +0.1%  | 50310 | −22.1% |
| 0,00  | 70589 |        | 70589 |        | 70589 |        | 64621 |        | 64621 |        | 64621 |        |

We claim:

1. A compound of the formula I

AcPhe-Aib-Ser-Aib-x-Leu-Gln-Gly-Aib-Aib-Ala-
    Ala-Aib-Pro-y-Aib-Aib-Gln-Trp-ol (SEQ ID NO. 1)

in which x and y, independently of each other, denote Aib or Iva.

2. A pharmaceutical composition comprising a compound as claimed in claim 1 and one or more pharmaceutical excipients.

3. A method for treating bacteria, fungi or nematode infections in a host comprising administering to the host a compound as claimed in claim 1 or a physiologically tolerated salt thereof in a pharmaceutically effective amount.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa stands for
            N- acetylphenylalanine (AcPhe)."

( i x ) FEATURE:
        ( A ) NAME/KEY: Modified-site
        ( B ) LOCATION: one-of(2, 4, 9, 10, 13, 16, 17)
        ( D ) OTHER INFORMATION: /note="Xaa stands for
            alpha- aminobutyric acid (Aib)."

( i x ) FEATURE:
        ( A ) NAME/KEY: Modified-site
        ( B ) LOCATION: 5
        ( D ) OTHER INFORMATION: /note="Xaa stands for
            alpha- aminobutyric acid (Aib) or isovaline (Iva)."

( i x ) FEATURE:
        ( A ) NAME/KEY: Modified-site
        ( B ) LOCATION: 15
        ( D ) OTHER INFORMATION: /note="Xaa stands for
            alpha- aminobutyric acid (Aib) or isovaline (Iva)."

( i x ) FEATURE:
        ( A ) NAME/KEY: Modified-site
        ( B ) LOCATION: 19
        ( D ) OTHER INFORMATION: /note="Xaa stands for tryptophanol
            ( T r p - o l )."

( x i ) SEQUENCE DESCRIPTION: SEQ ID NO:1:

Xaa Xaa Ser Xaa Xaa Leu Gln Gly Xaa Xaa Ala Ala Xaa Pro Xaa Xaa
    1                5                            10                        15

Xaa Gln Xaa